US006537772B1

United States Patent
Alarcón et al.

(10) Patent No.: US 6,537,772 B1
(45) Date of Patent: Mar. 25, 2003

(54) EQUIPMENT, KIT AND METHOD FOR MICROBIOLOGICAL DIAGNOSIS

(75) Inventors: Orestes Rolando Contreras Alarcón, Ciudad Habana (CU); Gloria Roura Carmona, Ciudad Habana (CU); Francisco Novo Mesegué, Ciudad Habana (CU); Silvio Hernández Ramirez, Longuevil (CA); Nardo Ramirez Frómeta, Ciudad Habana (CU); Iván Manuel Ramirez Molina, Ciudad Habana (CU); Angela Mariana Zayas Tamayo, Ciudad Habana (CU); Fernando Travieso Ruíz, La Habana (CU); Cheyla Romay Penabad, Ciudad Habana (CU)

(73) Assignee: Centro Nacional de Investigaciones (CU)

( * ) Notice: Subject to any disclaimer, the term of this patent is extended or adjusted under 35 U.S.C. 154(b) by 0 days.

(21) Appl. No.: 09/426,074

(22) Filed: Oct. 18, 1999

Related U.S. Application Data

(63) Continuation of application No. PCT/CU98/00004, filed on Apr. 20, 1998.

(30) Foreign Application Priority Data

| Apr. 18, 1997 | (CU) | ................................................. | 45/97 |
| Apr. 29, 1997 | (CU) | ................................................. | 48/97 |
| Jun. 6, 1997 | (CU) | ................................................. | 65/97 |

(51) Int. Cl.[7] .............................. C12Q 1/04; C12M 1/00; G01N 33/53
(52) U.S. Cl. ...................... 435/34; 435/975; 435/283.1; 435/968; 435/848; 435/849
(58) Field of Search ....................... 435/34, 975, 283.1, 435/968, 848, 849

(56) References Cited

U.S. PATENT DOCUMENTS

| 3,609,040 | A | 9/1971 | Kuzel et al. ................... 435/34 |
| 3,712,144 | A | 1/1973 | Kuzel et al. ................... 435/34 |
| 5,345,395 | A | 9/1994 | Griner ........................... 435/34 |
| 5,637,082 | A | 6/1997 | Pages ........................... 435/34 |

FOREIGN PATENT DOCUMENTS

| EP | 0304406 A | 2/1989 |
| EP | 333560 | 9/1989 |
| WO | WO 94 07123 A | 3/1994 |

*Primary Examiner*—Louise N. Leary
(74) *Attorney, Agent, or Firm*—Lackenbach Siegel

(57) ABSTRACT

The present invention is related to microbiology and forms part of a system for rapid microbiological diagnosis. The invention allows detection of turbidimetric changes due to microbial growth, using equipment comprised of two main devices: a static turbidimetric minireader and a microflow sensor which is fed by a peristaltic pump; this equipment is coupled to a microcomputer with a program package for acquisition, processing and formation of databases used in generating necessary reports.

The diagnostic kit has a glass vial with culture medium and a polymer with derepressive activity and two additional substrates for *E.coli* identification, as well as a set of antibiotic discs arranged in a strip for antibiogram determination from previously isolated colonies or samples obtained directly from their sources, allowing detection of urinary tract infections from direct samples of urine, and additionally simultaneous identification of *E.coli*.

20 Claims, 5 Drawing Sheets

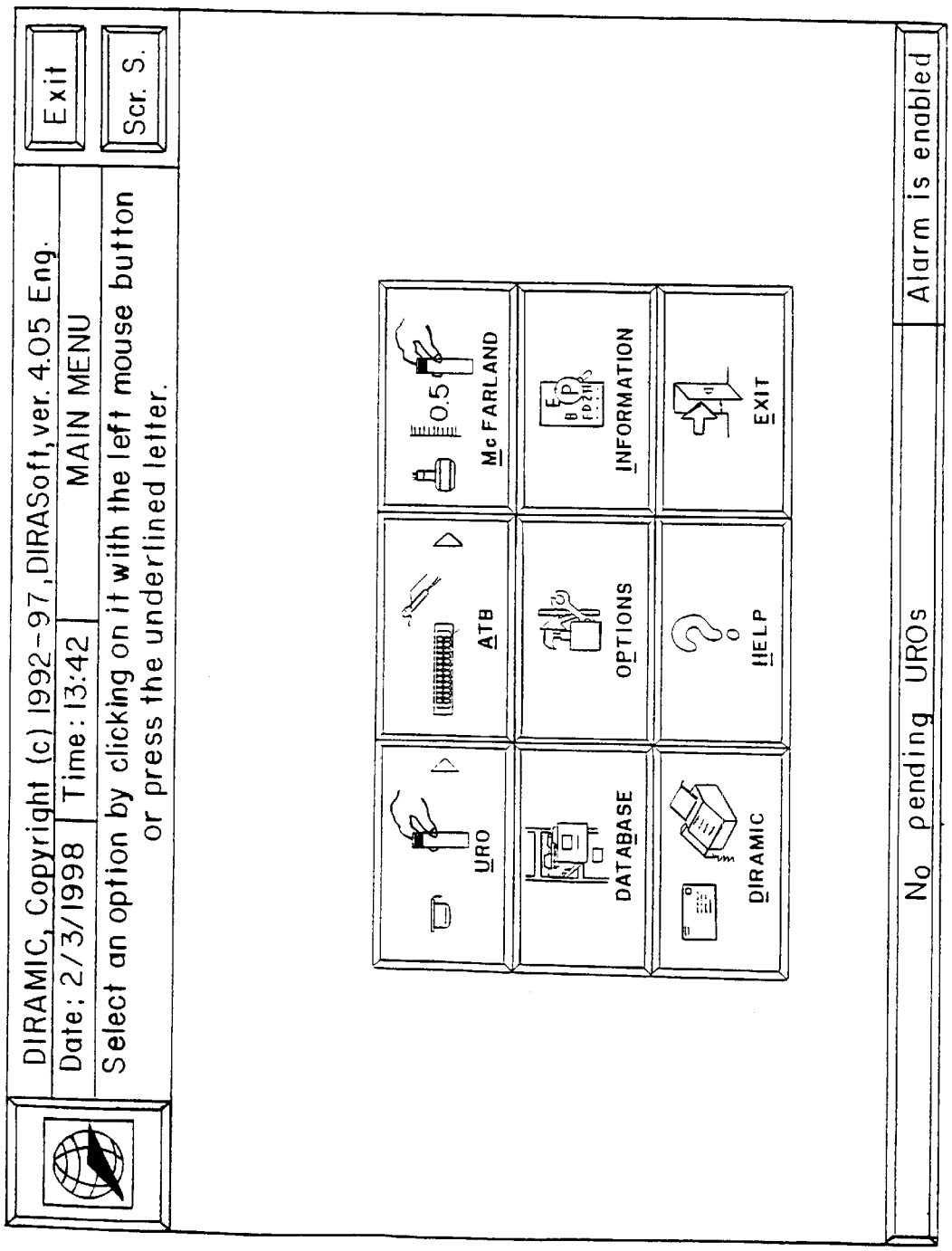
FIG. 5A Screen of Main Menu

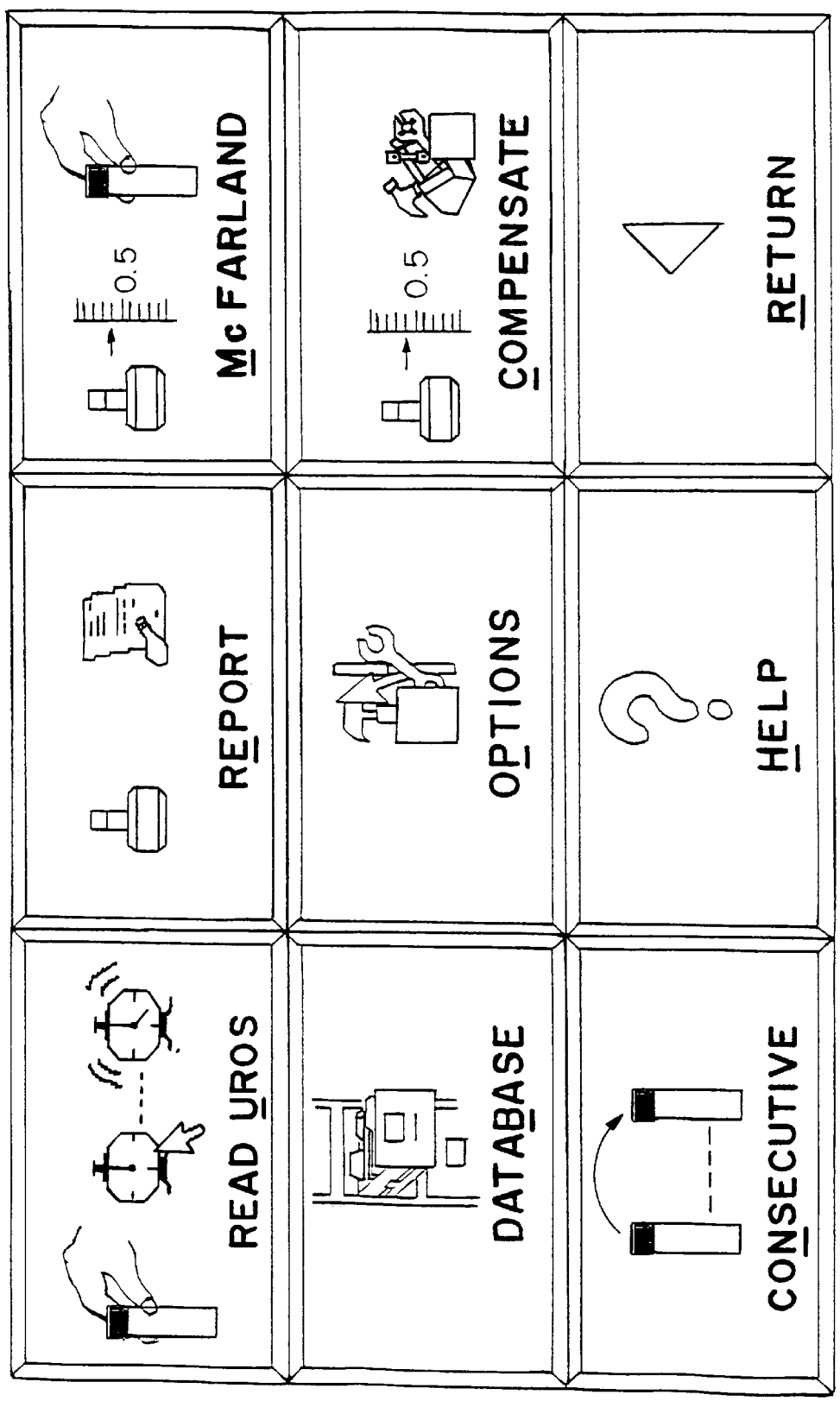
FIG. 5B  Screen of Menu of Urocultures

EQUIPMENT, KIT AND METHOD FOR MICROBIOLOGICAL DIAGNOSIS

This application is a continuation of PCT/CU98/00004 filed on Apr. 20, 1998.

TECHNICAL SECTOR. BACKGROUND OF THE INVENTION

The present invention relates to microbiological diagnosis, and more specifically to a method for rapid microbiological diagnosis, and the equipment in the form of a kit, which is used to perform this diagnosis. This diagnosis method has applications in human and veterinary clinical medicine.

PRIOR ART

Microbiological diagnosis is based on physical, chemical and biological methods that have been widely developed in previous prior art.

For example U.S. Pat. No. 3,506,544 describes an electrochemical method for detecting bacteria through measurement of the decrease in polarographic content of the oxygen which circulates through an electroanalytical cell that contains two different electrodes immersed in an inoculated culture medium. This method uses great quantities of culture medium (15–18 ml) for its analysis, thus making handling of the samples difficult on a routine level.

Another method that has been used to detect microbial growth is a method using a voltaic cell source, which is based on the use of an appropriate medium with electrodes of noble metals and predetermined volumes, that generate a potential which drops at the moment of growth of the bacterium. Other equipment using this principle has been described in the scientific literature. For example, the equipment described by patent GB 83-17685 uses the same procedure. This patent describes a method of detection that uses the variation of the potential between electrodes that are in contact with fluid samples. Thus lower potentials are measured with implied higher impedance at the opening which cause a change in the measured signal due to undesirable and unavoidable noises. In most cases the system uses electrodes of noble metals or no recoverable gold plated electrodes.

An efficient and simple method for detecting microbial growth is based on the measurement of conductometric changes that occur in a suitable culture medium due to the microbial growth. According to pertinent literature, ionic movements produce a signal of conductivity measurement of the solution in a cell that indicates the conductometric value of the solution.

It is known that conductivity cells do not have total lineal behavior in their baseline scale. In addition, analysis depends on temperature. In U.S. Pat. No. 4,482,967 a detector and a method to measure the conductivity that corrects these defects is described. This reference shows equipment of high accuracy and complexity with special provisions to measure absolute values of conductivity in a gas chromatograph, with conventional cells and large volumes.

It is known that microbial growth can be detected in fluid samples using different methods, for example, by using a turbidimetric method in which the bacteria growth produces turbidity that is read by the system detector and compared with established standards. This system requires conventional optical sensors, with high quality optical receivers, sample containers of complex design to work with samples that include visual solids. (for example, antibiotic discs) A disadvantage of this method is that is does not analyze impure samples, i.e. it requires homogeneous optical samples, because of the optical complexity of the apparatus system. U.S. Pat. Nos. 3,832,532, 3,895,661 and 3,889,011 describe methods and apparati based on these principles. U.S. Pat. Nos. 4,021,120 and 3,714,445 describe devices (turbidimeters) which measure the turbidity of microorganisms in liquid mediums.

U.S. Pat. Nos. 4,021,120 and 3,714,445 describe devices based on turbidimetric principle to measure the growth of microorganisms in liquid mediums. U.S. Pat. No. 4,021,120 describes a device to monitor the growth of microorganisms in a liquid medium that contains gas. Samples are taken from the medium, using a pump that carries the sample to a degassing chamber, eliminating gas bubbles. The sample is then introduced into a calibrated chamber through which a light ray passes. The light ray strikes a photoelectric cell, producing a current that is increased by an amplifier. This indicates growth of the microorganisms. The magnitude of this current will depend on the intensity of the light ray and will be influenced by the turbidity of the medium. The sample is then pumped back to the receiving vessel to be analyzed. This method of measurement, as well as one described in U.S. Pat. No. 3,714,445, is complex from an optical and mechanical perspective; in addition, the measurement chamber and the pumps and ducts used to transfer the samples should be sterilized frequently, this makes its use difficult in routine diagnostic methods.

Patent GB 2 221 986 and U.S. Pat. Nos. 3,819,278 and 4,725,148 refer to turbidmeters that directly measure the microbial growth using the same principle of previous methods. They present optically and mechanically complex systems that need sterilization between each batch of microorganisms.

On the other hand, U.S. Pat. No. 3,832,532, also uses an conventional optically device that includes a cuvette of spectrophotometric quality, the device takes measurements using antibiotic discs included in its design as an interconnected bi-lobed chamber. After the incubation is completed, the liquid must pass to the other chamber for measurement, in order to avoid presence of the antibiotic disc during the reading step.

Thus the invention of U.S. Pat. No. 3,832,532 presents a system of operative and technical complexity and in addition has economical implications.

The present trends of microbiology make use the search of procedures that allow rapid identification of microorganisms (between 2–4 hours) in biological samples. To accomplish this, different strategies have been used, among them the use of specific enzyme markers.

According to the present state of the art, most of the biological samples cannot be used directly; isolation and growth of the microorganism must be completed before the sample can be identified, requiring 24–48 hours of laboratory time.

Infections of the urinary tract are considered one of the most prevalent among infectious illnesses.

The classic technique for detecting bacterial infections in urine requires cultivation on plates for at least 24 hours in order to discard all negative samples and to select positive ones.

Only 20% of the urine samples that arrive at the lab are positive, and from these 70% correspond to infections provoked by *E.coli*. Identification of *E.coli* saves time and resources, as only 30% of the positive samples would be isolated for identification.

According to the state of the art, identification of *E.coli* is accomplished mainly by two specific enzyme markers for this bacterium, β-D-glucuronidase and tryptophanase enzymes, through Indol formation (Kovacks, N. Eine vereinfachte Methode zum der Nachweis der Indolbildung durch Bakerien. Z. Immunitatsforsch., 55; 311–315, 1928). 94% of all *E.coli*, a few Salmonellas and Shigullas show positive reaction towards β-D-glucuronidase. Indol formation is positive for 99% of all *E.coli*; thus combination of both tests allows unmistakable identification of this microorganism.

Presently, different tests are being marketed, like BACTIDENT-*E.coli* and different culture mediums like FLUOROCULT-MUG, (both from MERCK DIAGNOSTICA). They are based on the above principle. In order to use them, an isolated colony from a previous isolation of the microorganism used to make the BACTIDENT identification must be taken; or the sample can be inoculated into the culture medium and grown for 24 hours; it is only possible to detect associated changes to the specific substrate transformation (FLUOROCULT-MUG).

A solid culture medium for simultaneous detection of coliform bacteria and/or *E.coli* in water samples and in foods is reported in the patent application No. WO 95/03424. 24 hours of incubation is required after inoculation of the plate with the sample to be evaluated. Similar procedures are followed in the Diagnostic Kit URILINE ID and the culture medium CPS ID, both from BIOMERIEUX, France. The incubation of the samples on solid medium for 24 hours is necessary before identifying the microorganism in both cases. The patent application No. WO 80/02433 refers to a procedure to identify bacteria through the combination of different tests to determine 26 bacterial enzymes; among them β-D-glucuronidase and tryptophanase are useful to identify *E.coli*. In the present invention, bacteria should be isolated from the clinic specimens before their identification.

DISCLOSURE OF THE INVENTION

The objective of the present invention is to provide a system that allows detection of microbial growth early in samples obtained directly from animals, plants and their fluids, on which detection of growing microorganisms is determined through the use of micro-samples. This system is based on the detection of turbidimetric changes in a culture medium, produced by the growing microorganism. This system includes equipment, a diagnostic kit and a method designed for this purpose.

The uniqueness of the present technical solution is that it allows detection of infected samples obtained directly from the species that produce them.

Additionally, among other applications, the present invention permits obtaining the sensitivity pattern to the different antibiotics of microorganisms using previously isolated colonies or positive samples of urocultures and hemocultures, saving time required for isolation and purification processes.

In the particular case of urinary tract infections, the present invention allows discrimination of positive samples from negative ones using direct urine samples, even if contaminated with other bacteria. It can also include the simultaneous identification of those infected samples, specifically with *E.coli* bacterium.

Following the system of the invention, more than 1000 tested samples have shown a 95% correlation with the total count of viable cells in CLED culture medium; this method is conventionally used to detect urinary tract infection.

In the antibiogram determination, the correlation with Bauer-Kirby method is 92.4%, major errors 1.3%, and very major errors 0.4%.

In the determination of the antibiogram, the correlation with the Bauer-Kirby method has been established as a 75.8% predictive value for the sensitive antibiotics and an 85.9% for the resistant antibiotics, obtaining an overall sensitivity of 80.6%. The system guarantees a 90% effectiveness for the detection of sensitive antibodies.

The present invention provides useful information related to medical microbiological diagnosis in a short period of time. This information is very important to prevent the improper use of antibiotics, the development of microbial resistance, long hospital stays and death in the case of serious infections.

The system is characterized by its speed; a urine infection can be determined in a period of four hours and on positive samples reliable antibiogram results can be obtained.

At the same time this system is highly accurate in a significant manner. The obtained results can be verified as necessary.

From the social point of view, the system has a great importance because of the possibility of providing antibiotics in a prudent and beneficial way, as well as avoiding is long hospital stays. From the ecological point of view, the invention reduces the development of bacterial resistance. It is a highly flexible system, in which adaptation of the information can be altered according to the needs or requirements of the users. The system offers the possibility of changing the use of the antibiotics according to the particular needs.

The system of the present invention comprises equipment, a diagnostic kit and a method designed for rapid microbiological diagnosis, which can be applied to human and veterinary clinical medicine.

The equipment has been designed to work with large numbers of samples and uses not only an operative program, but also a functional interface between man and machine. It also provides an audiovisual alarm to signal readiness for a reading and to avoid operational mistakes. The software package for making measurements with this equipment can be installed in the free slot of a computer.

The equipment of the present invention includes the following devices:

A control module which is incorporated in a personal computer.
An interface card.
A peristaltic pump.
A sensor.
A calibrator.
A printer.
An ultraviolet (UV) lamp which may be optional.

The personal computer should have the following properties:

IBM Compatible, 386/486, 25–66 MHz.
RAM memory, minimum 1 megabyte.
Hard Disc, minimum 40 megabytes.
Floppy Disc 3½", optional.
Display SVGA Color.
Keyboard, Mouse and Printer.

The peristaltic pump has been designed to produce circulation of the samples through the sensor. Its cassette can be set easily, allowing a regulated and uninterrupted flow and may be used independently or incorporated with the system. The pump flows at 2.0–2.6 ml/minute and is fed either 220 vac or 12 vdc. Its potential consumption is 0.5 watts.

A reader connects the sensor to a continuous microflow, which is used to detect turbidity changes due to microbial growth in previously prepared samples coming from different sources. The sample size may be of very small volumes (up to 200 microliters) and may be In movement,—i.e. in a moving liquid, where samples can or can not be influenced. Using the present invention it is not necessary "to clean" the flow reader during measurements, thus minute samples can be measured continuously. This measurement is not influenced by turbidimetric variations of culture medium as a consequence of the changes of the samples; however the invention allows detection of small variations of medium turbidity due to microbial growth. Temperature control is not required for the measurements. It is also possible to make an unlimited number of measurements of different samples from different sources and microbial cell concentration.

Calibration of this sensor is unique as it is automatic and operates with a continuous flow of 2–2.6 ml/minute. Optic range of measurement is 0.00–2.00 McFarland units.

The present invention uses a calibrator based on nephelometric techniques and uses the McFarland scale. It joins together a direct light source and a photosensor and is adjusted through a program. The calibrator measures the turbidity in Mueller-Hinton liquid medium up to 0.2 McFarland units. Energy requirement is 5 vdc and consumption is 50 ma.

The UV lamp that is coupled optionally to the equipment allows identification of the bacterium *E.coli* in tested samples. The program offers a simple man to machine interface, is easy to manage and allows the selection of different options of bar-menu or keyboard function, combined with icons, as well as automatic data storage. It uses a structured interrogative language (SQL) for obtaining information and an external utilities 'BACKUP' which makes secure copies.

The program has an alarm system to be used in case of obstruction of the opening, an audiovisual alarm to control the reading time of each sample, as well as other utilities for technical maintenance.

The essential unique features of the equipment of the present invention are the turbidimetric static minireader, the microflow sensor which is fed by the peristaltic pump, and their connection to a microcomputer with a program package for acquisition, processing and creation of data bases, used to generate necessary reports.

FIG. 1 shows the general overview of the integral plan of the equipment of the present invention. As shown, this equipment comprises a turbidimetric reader of microflow (1) which is fed by a peristaltic pump (2) and adjusted to electronic equipment of high sensitivity (3) that detects turbidimetric changes of microflow (1) through a measurement method that allows use of a group of algorithms to detect small turbidimetric variations and to properly process obtained data. It is formed by a turbidimetric measurement circuit (4) connected through an interface card to a central processing unit (5). This unit receives all keyboard commands (6) and delivers the results in a display (7). It can detect smallest variations of turbidity that occur in the culture-inoculated medium in the sample that will be tested.

FIG. 2 shows a detailed design of the internal structure of the turbidimetric reader (1) where the variations of turbidity are detected. The procedure for measuring is very simple: the small opening of the reader (8) is introduced into the sample to be tested which then circulates through the reader with help of the peristaltic pump (2) of FIG. 1. This peristaltic pump works continuously throughout the measurement. First the presence of the sample is detected by obtaining a voltage value that exceeds a pre-designated value and after a specified period of time the measurement is completed. As the peristaltic pump (2) in FIG. 1 continues to operate, there is a period of time between each measurement during which air circulates through the turbidimetric reader (1). This period of time is considered as the moment in which the turbidimetric reader (1) is cleaned. It is not necessary to make the additional step of washing in order to sterilize all parts of the reader.

The measurement chamber is composed of a plastic tube (9) introduced in a glass capillary (10). The light pass (11) is the orifice diameter through which the light coming from the photoemissor (12) should travel to reach the measurement chamber (9 and 10). The intensity of the luminous radiation, transmitted through the measurement chamber (9 and 10) will depend on the turbidity grade of the sample and is measured by a photodetector (13). The radiation produced by the photoemissor (12) is stabilized by means of an electronic circuit of conventional automatic control.

FIG. 3 shows a flow diagram using the turbidimetric reader. First the presence of the turbidimetric reader is verified by means of the subroutine of detection. If present, the existence of the peristaltic pump is checked, since the pump is necessary for the operation of the turbidimetric reader and for the cleaning process subroutine; the subroutine also establishes the required operational flow. The cleaning subroutine is important as the reader's parameters depend on the cleanliness of the measurement chamber. This aspect influences its effective life span.

After all the working parameters have been regulated, the turbidimetric reader will be ready. Any subroutine that is not functional will disable the reader. The main application of this device is directed toward the antibiogram determination of the sample, (antibiotic microorganism susceptibility), which is achieved between 2 and 6 hours, supported by a diagnostic kit designed for these purposes.

The other device that is incorporated into the equipment of the present invention is the static turbidimetric minireader mentioned before. It detects turbidity changes due to microbial growth in the sample developed in a glass vial containing liquid culture medium, one of the components of the diagnostic kit of the present invention. This vial is precisely fitted to the reading shaft of the equipment. The device is adjusted to use the vials for the direct reading of the sample; special cuvettes are not necessary to determine readings, making it possible to use in routine diagnostic mediums. The device calibrates the inoculum that is used in the diagnostic kit for detecting the antibiogram. It reports turbidity in McFarland units, according to latex patterns of NCCLS standards in an established range of measurement (0–4.0 McFarland units).

The diagnostic kit of the present invention is comprised of an 8-ml nephelometric vial that contains 4.5 ml of culture medium; the vial is made of autoclaveable borosilicate glass with a plastic cover.

FIG. 4 shows the components of the diagnostic kit of the present invention, consisting of a vial containing culture medium and the polymer, the strip support and the strip used for antibiogram determination of the tested sample. Modified sterile Mueller-Hinton Broth OXOID, pH of 7.4+/−0.2, together with a polymer, is used as culture medium in order to follow microbial growth.

The diagnostic kit used for detecting antibiogram in a sample utilizes antibiotic discs available commercially. They can be used in conforming designs that change according to need. Antibiotic discs are organized into non-transparent strips containing two free positions for negative and positive controls, which are filled with only culture medium and inoculated culture medium respectively.

They are used to calculate the growth index in the tested samples. There are 10 to 22 additional positions where antibiotic discs could be placed.

The program created for these purposes allows the introduction of these changes in the acquisition and editing processes. The kit has high flexibility and permits adaptations according to different needs. A polymer, that could be any linear polysaccharide of structural formula CH3-CH3-CH3-N or somewhat similar with molecular mass between 50,000 and 150,000, is added to the glass vial containing culture medium for dilution, forming part of the diagnostic kit of the present invention. The incorporation of this polymer into the culture medium, at a concentration between 0.05 and 1%, allows elimination of the inhibitor effect of catabolic products accompanying the tested sample inoculum; greater growth indexes of the infection-involved bacteria are obtained in a shorter period of time, in comparison with the required time when the same culture medium is used without said polymer. This new element in the diagnostic kit reduces false sensitive results obtained in susceptibility studies, and at the same time improves the correlation with Kirby-Bauer method of reference (Bauer, A. W.; Kirby, W. M. M.; Sherris, J. C. and Turck, M. An. J. Clin. Pathol. 1966, 45, pages 493–496).

Considering that this polymer can be metabolized only by a reduced number of microorganisms which are generally not found in analysis where the present system is applied, it is inferred that the bacterial growth effect is motivated by an inhibition of the repressor agents which are present in the culture medium. For this reason the said polymer should act by absorbing the catabolites which are involuntarily incorporated together with the inoculum that is analyzed. It has been observed that during the microorganism growth measurement process, after the said polymer neutralizes these catabolites, the bactericidal activity of tested antibiotics is more specific.

One of the advantages of the present invention is the fact that the system allows diagnosis of not only previously isolated strains but also direct samples of positive hemocultures, urine, etc.

First the sample is placed in the glass vial containing the polymer and the culture medium, immediately after the turbidity is determined (t0) and this value, along with the reading time according to the adjusted number of each sample, is fixed by the employed program. The vial is then incubated between 2 and 5 hours at a temperature between 35 and 37° C. At the end of the incubation the system emits, according to the programmed routine, a beep alarm sound and screen warning indicating that the sample should be read again. The samples that show increments higher than 0.08 McFarland units are considered positive samples.

Once positive samples are detected, the system of the present invention allows determination of their antibiogram in a very short time. For that purpose, an aliquot of the sample is transferred to a new dilution vial that contains fresh culture medium, which is distributed in the strip containing two controls (positive and negative) and from 10 to 22 antibiotic discs. After a 4-hour incubation period at a temperature of 37° C., the strip is read by placing the microflow sensor in each microwell, following the program instructions, which selects the moment of each measurement in series. Thus the influence of the previous reading is eliminated. From the obtained density values, the growth indexes are calculated (in the controls), as well as the inhibition percentage for each sample by each antibiotic. According to the inhibition level shown by the samples, the criteria of resistant, intermediate or sensitive, are adjusted among inhibition values in a range of 60 to 100%. This means that those samples with inhibition percentage smaller than 60% can be considered resistant, those showing values between 60 and 80% can be considered sensitive at an intermediate level and those which are inhibited between 80 and 100% are considered sensitive to the antibiotic tested.

Each result is checked in order to ascertain if it is between a minimum or maximum admissible growth (satisfactory antibiogram). The obtained results and edit data of each sample automatically create the corresponding databases.

As was previously noted, when applied to urocultures, the invention permits analysis with direct samples in liquid medium, read in commercial vials, and then executes antibiogram in positive samples. This process is completed in less than 9 hours, avoiding previous steps of isolation and purification of the samples and obtaining sensitivity levels greater than 90%.

This system also allows facing generated conditions due to the contaminated samples as well as the infection caused by more than one bacterium. The contaminated condition has been overcome, adjusting the magnitude sign and the time for detecting internationally accepted infected levels (>100,000 ufc/ml). This way, contaminated samples that are not infected are excluded from further processing because their smaller bacterial levels (<1000 ufc/ml) allow detection of contaminated samples only when they are infected. Taking into account the fact that the contaminated species are generally saprophytes, that, according to gram reaction, are sensitive to all antibiotics, in this particular case, it is evident that they cannot influence the detection of the resistance pattern of infected strains. These agree with the distinctive characteristics of the present invention.

In the case of infections produced by more than one bacterium, two situations could be presented. First, one of the infecting bacteria could predominate due to a greater specific growth rate after the minimum time of incubation; in this case the antibiogram will be accepted. Secondly, where both bacteria grow at the same rate, the antibiogram could show one effective antibiotic for both, or a plan of absolute resistance could be presented. In this case a new antibiotic could be tested and the sample should pass through isolation and purification procedures.

This collective analysis and rapid solution for each particular situation is possible due to the application of the reading concept in direct samples with high level of interference, in a brief amount of time and fixed aspects that characterize and distinguish the system of the present invention.

In addition to reporting detection of urinary tract infection and infecting bacterial susceptibility pattern, bacterial identification should be incorporated in order to produce a complete report. In order to achieve this goal, to the vial containing culture medium and polymer used for detection of urinary infection, two substrates that allow rapid identification of *E.coli* bacteria in urine might be added into the same detection vial, as has been stated before.

In the present invention, a designed culture medium that could be used in the proposed system allows detection of *E.coli* from infected urine samples tested after 4–6 hours of incubation time.

Proposed culture medium in the present invention include per liter, more than conventional nutritive bases included in Oxoid Mueller Hinton culture medium: Meet infusion, 300 mg; casein hydrolyzate, 17 g. and starch, 1.5 g., substrates as MU-β-glucuronide (0.1 g), L-tryptophane (1 g), and used polymer with de-repression activity (1 g). All of these components are soluble in potassium phosphate buffer 50 mM, and medium pH is adjusted between 7–7.5. The medium is then distributed by volumes of 4.5 ml into vials that are sterilized by autoclave for 20 minutes at 121° C. The previous substrates are useful for detection of MU-1 β-D-glucuronidase and tryptophanase enzymatic activity produced by *E.coli*. For the last enzyme, Indol detection is needed. As such, after bacterial growth is obtained in the medium, an auxiliary reactive is added for activity development (modified Kovacks chemical reactive), whose formula is paradimethylamino benzaldehyde (2 g), ethanol and concentrated chlorhydric acid (20 ml).

Signals of enzymes-substrate interaction are detected, as a first step by exposing vials with turbidity increment (positives), to a UV light source (item that optionally could be included with the equipment of the present invention), for detection of fluorescence that is generated from released β-methylumbelliferone. As a second step, Indol production is tested in the same vial by addition of Kovacks modified reactive.

WORKING EXAMPLES OF THE INVENTION

Example 1

Turn on the equipment:

15 minutes before starting a reading, turn on the equipment. After the computer is activated, the auto-execution program goes directly to the program designed for the execution of all process; in this way initially, it will test the existence and integrity of the database and check functioning capacity of each one of measurement module components: sensor, inoculum calibrator and peristaltic pump. Also, it will check electronic key existence that is coupled to a parallel port of the computer. The program will inform about any mistake detected in any of system elements and will disable related options. If a database had not been created, it will be created if the user makes this decision. If there is no database, it will be created if the user decides to do it.

Example 2

Sample preparation for uroculture tests:

Uroculture is a well known test, used to screen urine samples for infection.

Procedure starts by measuring optical density immediately after vials have been inoculated (T0h), followed by a second measurement 4 hours after incubation (T4h).

The measurement is made photometrically by using an inoculum calibrator. The following steps show the entire procedure:

1. A 4.5 ml sterile culture medium vial is inoculated with 500 μl of urine.
2. Initial turbidity is measured in McFarland units, using the inoculum calibrator (T0h).
3. Sample is incubated at 37° C. for 4 hours after which the equipment emits a sound alarm for each sample.
4. A measurement of turbidity of inoculated vial is made after 4 hours of incubation (T4h), and according to the level of detected increase, samples are classified as positive, negative or doubtful. In the last case, the sample should be checked after one additional hour of incubation. Also patients with antecedents of renal disease should use the same procedure as before (T5h).

According to needs, when all measurements have been completed, edition of each case could take place and stored in the system database. If the automatic printer option is activated and printer is ready, cases will be printed automatically. Samples classified as positive are ready for antibiogram detection.

Example 3

Procedure for antibiogram:

For antibiogram, strips of 12 to 24 microwells are used. The first two are for positive (C+) and negative (C−) controls, respectively; antibiotic discs are placed in the other microwells.

Strip inoculation is done by sample distribution in the first microwell and in those with antibiotic discs. The second microwell is filled with sterile culture medium.

Example 4

Inoculum preparation:

From a pure strain:

If inoculum is prepared from a pure strain, the following steps should be executed:

1. Three or four colonies from a fresh culture medium (18–24 h) are taken and added to sterile 4.5 ml of Mueller Hinton broth reinforced with lineal polymer, molecular mass 50,000, until a 0.5 McFarland scale unit is obtained, by mininephelometer testing. An option that appears in principal menu (McFarland).
2. From this cell concentration 150 μl are added to 4.5 ml sterile culture medium placed in the other vial, and homogenized by stirring.
3. From the last dilution 200 μl (0.2 ml) are distributed in the strip for antibiogram, in the microwells used for positive control (C+) and those with antibiotic discs.
4. In the second microwell, used for negative control (C−) 200 μl (0.2 ml) of sterile culture medium are distributed.
5. Once finished, the strip is sealed and incubated at 37° C. for 4 hours.
6. Strip is taken from incubator and after 10 minutes at room temperature, readings start. Manual or mechanical stirring is recommended for strip homogenization.
7. The strip is opened and the reading begins.

The difference between (C+) and (C−) in the antibiogram reading must be between a given value defined by the Admissible Minimal Growth The antibiogram must be repeated if inhibition levels are consistently low (antibiogram not reliable) in the presence of the values next to the differentials established by this parameter, or are detected in each one of the proven antibiotics. In these cases reduction of volume is recommended until reaching is 30% of the volume of the inoculum used previously.

If the inoculum is prepared from a positive uroculture, an accurate method for acquiring its antibiogram is to dilute the sample until reaching 0.5 on the McFarland scale; once reached, the desired turbidity is found by continuing the process from point 2 as described previously for the acquisition of the inoculum from a pure strain.

If a positive uroculture is detected in 4 hours and if it has a value less than 0.5 on the McFarland scale, this uroculture must be incubated until said value can be reached or it can be spread in a culture medium, to be analyzed the following day. This may be due to:

1. Low amount of non-infecting microorganism.
2. Patient receiving antimicrobial therapy.

When the inoculum is prepared from positive hemocultures (18 to 24 hours of incubation), the following steps should be taken:

Extract the upper layer of the hemoculture (supernatant) 200 µl; add to 4.5 ml of culture medium Mueller-Hinton+POI-10.

Read the turbidity in the mininephelometer using the option "McFarland" on the Main Menu, and monitor until values of 0.5–0.7 on the scale are reached.

The process of point 2 described previously is continued the same as for the acquisition of the inoculum of a pure strain.

Example 5

Program Applications.

The invention supplies a set of full interactive programs to carry out the Antibiogram and Uroculture tests. Data obtained in each test can be stored in the database for further processing. The user is guided in an easy-to-operate environment that does not require previous experience in computer operation.

Each test is dealt with in independent menus that form a Main Menu.

To access any of the system's options:

1. Press the key that corresponds to the underlined letter in the desire icon.
2. Or place the mouse pointer over the selected icon and press the pointer's left button.

To cancel the selection option, press the "ESC" key or use the mouse to select "Return" or "Cancel" to return to the previous option or cancel the operation.

Main Menu

Once the system is set up, the program will show the Main Menu, which is the starting point for all the operations.

The main window of the menu is composed of three basic panels:

Central panel that shows the icons which activate the main options of the program.

Upper panel that shows information related to the system's version, date and time, current menu and a brief explanation of how to choose a new option. The upper panel supplies two special options found on its far right corner:

Exit: Used to stop the program at any time as long as a measurement or a critical operation is not running. Use of this option is recommended. DO NOT TURN OFF THE COMPUTER while the program is running to avoid eventual software malfunctions.

SCR.S.: Allows the user to manually activate the system's Screen Saver when the instrument is to be left in a standby mode; this avoids screen damages that can occur when a steady image is left during long periods of time.

Note: This option will be activated automatically if the system is left inactive for a certain time. To return to a normal screen, move the mouse or press any key.

Bottom Panel: Shows information about the uroculture test. If some tests are waiting to be read, they can be sorted by the "next reading" option, and the amount and the time at which the first one should be read is shown. The bottom panel also shows whether the system's uroculture reading alarm is activated.

Main Menu Options

The principal menu is linked by a set of icons containing drawings related to the operations that are performed when these are activated. A black triangle pointing right in the options "URO and ATB" is an indicator that identifies the presence of a submenu with additional options.

Nine icons define the available options within main menu, controlling all the actions of the system.

These are:

URO: Activates the icons menu of uroculture.
ATB: Activates the icons menu of the antibiogram.
McFarland: Permits measurement of the contents of the vial in the calibration unit (McFarland scale).
Database: Permits access to the database of antibiograms or urocultures.
Options: Changes configuration of the system.
Information: Shows administrative information of the system.
DIRAMIC: Lists the address of the manufacturer of the system.
Help: Gives information about the current option.
Exit: Abandons the system.
Menu of Urocultures
Uro: Menu of Urocultures Upon selecting the URO icon of the main Menu, a sub-menu with a new set of options will be provided for measurements of Urocultures. Within this menu the following options are provided.

Description of the options of the Urocultures Menu:
Read Uros

Procedure for the reading of to be urocultures. Upon activating this option, a list of the uroculture cases waiting to be read is displayed, where the consecutive case number, the time that must elapse between readings and the date and time of the next reading, are shown. If the list is empty, no cases are pending.

To select a specific case from the list, press the left mouse button twice quickly (or press the keyboard's space bar) while pointing the case. The selections will then appear with check marks by their sides; the majority of the operations will apply only to them. The "READ URO" selection will provide the following options:

New uros: Allows reading of the TOh (first reading) of the cases of uroculture. If the McFarland calibrator has not been previously set, the program will ask the operator to place a sterile culture medium flask in the well of the calibrator to set the zero reference before adding new cases. Once the reference point of the McFarland calibrator is set, a message window will show its results. A "Compensation Factor" will evaluate the performance of the calibrator. Any value below 2.5 will be accepted; however, values beyond 2.0 might be an indicator of dirt in the measuring well. In such cases, the well should be clean with a small piece of cotton fabric dampened in ethyl alcohol. Subsequently, a window will show selection options of reading, editing, or changing the time that must elapse between readings (TO–TFh). This last option must be set before the second reading is done.

Re-read: Allows repeat of the reading of time TOh of a sample. This option is useful in correcting an error in the reading of one of the cases. When activating this option, a window with the same selections as the "New uros" option will be shown plus a new choice for moving to the "Next" case without modifying the current one.

Edit: Allows filling out a form with the general data of the patient. Another group of fields gathers information of interest for the laboratory. In order to save the data that has been typed, the left mouse button can be pressed on the desired option. Alternatively, use the "RETURN" key to accept or the "ESC" key to abort the edition process.

When editing several cases, the option "Next" will become available. With this option the edition of the current case is abandoned and the action moves to the next case. If the option "OK" is selected, the data set will be stored and the next case will be automatically presented for edition. A field marked by a black triangle pointing down indicates that when this field is selected, a pre-edited list will appear in order to select the desired text. A selected search is possible by typing the first letters of the searched word. This edition style is used to standardize the text corresponding to important fields, avoiding spelling mistakes that could confuse a "Search" process. Words in this list can be deleted, modified or added, but if a text element of the list is modified, the complete database will be modified accordingly.

To move from one field to another within the edition process, press the TAB key or simply press the left mouse button on the desired field.

If several cases are simultaneously selected for edition, a "Next" option will become available. This option ignores the changes made to the current case and moves to the following. However, if the option "OK" is selected, the current data will be saved to the database before the next case is presented for edition.

TO–TFh: Allows the user to set the time that will elapse between the first and the subsequent reading. This option will be executed for all the selected cases whenever possible.

Note: If the time that has been set is shorter than the time that has already elapsed, the system will send an error message.

Cancel: Allows the user to delete undesired pending cases. This option will be executed for all the selected cases.

Read TFh: Allows execution of the final reading of a uroculture in order to obtain the result of the test. Upon activation of this option, a window will appear, displaying the general data of the case and its classification as "Positive, Negative or Doubtful." To accept this reading select "Read." If the option "Next" is selected instead of "Read", the results of the current case will not be considered as final and the action will move to the next selected case. This option is used when the operator decides to increase the time between readings in order to study the evolution of a specific sample.

Select:: Allows selection of all the cases in the list.

Sort: Arranges the list by the consecutive number or by the time of next reading. This option is useful when it is desirable to sort the cases according to the time when they are to be read, which does not always coincide with the consecutive order.

Print: Supplies information for configuring the output of data to a suitable printer.

The following options can be selected:

Printer: Allows the setting of a specific type of printer:
Epson: For standard dot matrix printers.
HP Laserjet:: For Laser printers.
Adobe Script: For PostScript printers.
ASCII: To write data to an ASCII file. If this option is selected, the name and path of the text file where data is stored may be specified.
Cancel: Returns to the previous option.

Copies: Number of copies that will be printed.

Lines/Page: Number of lines of text on each page.

Print to: Allows selection of the output port of the computer where the printer is installed, usually LPT1, LPT2, LPT3 or LPT4.

Return: Returns to the previous option. The available commands within this option are:
OK: Starts printing. After activating this option, an information message about printing choices will be displayed. The possibility of canceling the printing is included.
Cancel: Cancels the operation.

Return: Transfers the control to the UROCULTURE MENU.

Report
Generates a report with the results of the uroculture test. This report may be printed.

McFarland
Allows the measurement of microbial growth in McFarland units according to NCCLS standards, taking as zero growth reference a non-inoculated sterile culture medium. Graphic scale and digital mode show the readout. The second figure of the digital values should be seen and understood only as a reference of the trend of the sample. Additionally, an approximate cell count, obtained by mathematical calculations in accordance with NCCLS standards, is supplied.

To perform the measurements, the outside surface of the flasks used in the calibrator must be clean and free from scratches.

In order to increase precision, a flask that is measured in the McFarland calibrator should be marked in such a way that its position can be easily repeated each time the flask is read. The mark should always be visible to the operator. Two commands are available within this window:

Compensate: By choice of the user, this action sets the 0 McFarland reference for microbial growth readings of the sample flasks. It can be useful if a different batch of culture medium is going to be used after the calibrator is compensated. The process is achieved by placing a flask with a non-inoculated culture medium in the measuring well of the McFarland calibrator.

Return: Returns to the previous option.

Database
Using this option, a study and printing of stored Uroculture cases is possible. The stored data can also be modified by choice of the user. The database can be queried by specifying the content of one or several fields in one search.

In the upper part of the window, the case number of the current data is shown. The total number of cases in the database (Example: Case 1 of 100) and the display mode are also reported.

The display mode refers to the way data was extracted from the database: if the option "Browse" was used, "All the cases" will be reported, but if a searching process was applied, "Search" will be reported and only those cases matching the search conditions will be available. The term "Viewing" will be reported if the displayed data corresponds to "General data" or to the final "Results" of the test.

Once "Database" has been selected, the following options will be available inside the window:

First: Displays the first case of the database.
Previous: Displays the case that is before the current case.
Next: Goes to the case after the current case.
Last: Jumps to the last case of the database.
Go to case: Jumps to a selected case number.
Data/Results: Switches the shown data from "General data" to test "Results."
Edit: to edit the general data of the test.
Search/All cases: This option switches the viewing mode from the results of a "Search" process to "All cases" available in the database. Upon selecting the Search mode, a window will be opened allowing the operator to restrict 14 fields of the database in order to meet specified requirements of the query. Each option will supply a menu where the search criterion for the selected field can be chosen. Three commands can be used within this window:
Search: Allows start of a search or query according to a pre-defined set of field restrictions.
New: Formulates a new search or query under different restrictions.
Return: Returns to the previous window.
Some of the available "Search" criteria are now explained:

Containing: Allows searching without taking into account whether the field was typed in upper or lower case. It also allows search for words or syllables contained in a word or phrase; for example: "infect" in severe infection.
Non containing: Performs in a similar way as the "containing" option except that it will exclude those cases that meet the specified condition.
Included in list: Allows creation of a list with the desired requirements. This criterion is used when searching for several bacteria. Upon activation of this option, a list of elements that can be added or deleted will be displayed.
Not included in list: Similar to the "included in list" option but excluding the cases that meet the desired condition.
Ignore: Ignores the selected field during the search process.
Exactly as and different from: Compares exact words, considering if they were typed in upper or lower cases. Two identical words, one typed in upper case and the other in lower case, will look different to this search option. To make a search that will not consider this condition, use the "containing" or "not containing" option as convenient.
Print: Produces a printout to a specified printer or to an ASCII file.
Return: Returns to the UROCULTURE MENU.
Options
Allows the following possibilities:
Automatic printout after antibiogram measurement.
Enable or disable the uroculture time-out sound signal.
The use of colors in the screen report.
The time that will elapse between first and next uroculture readings. (program default is 4:00 hours)
Compensate
User choice to set the 0 McFarland reference for microbial growth measurements. The procedure is carried out using a vial containing un-inoculated culture medium.
Consecutive
Allows setting the consecutive number for the new cases of uroculture whenever the setting does not influence an existing unread uroculture.
This option becomes useful when it is required for starting the uroculture counter in a number different than 1; for instance, to start from 50, 100, etc.
Note: The program handles the Consecutive number as the "consecutive of the day." When a change of date is detected, the system, by default, will set the consecutive number to 1.

Help
Shows user information about the system and each of its options and operations.
Return
Returns to the MAIN MENU.
Antibiogram Menu
ATB: Antibiogram Menu.
Upon selection of the ATB icon in the Main Menu, an additional sub-menu with 12 basic operations required for this test will be supplied.
Description of options:
Read ATB
Allows the reading of an antibiogram that will determine the antibiotic susceptibility pattern of a given bacterium.
As a first step, the system will automatically check if the sensor has been rinsed and compensated and if the peristaltic pump is working properly. This procedure is hidden from the user if no problems are encountered.
Any detected malfunction will be communicated to the user.
When the first ATB of a day is going to be executed, the system will proceed in order to compensate the electronic operation point of the microflow low sensor. To accomplish this requirement, a totally interactive step by step procedure will guide the operator through the process.
Once the adjustment is finished, the system will send a report with the "Compensation Constant", which is a numerical value that will be normally found below 2.00. However, values between 2.00 and 2.50 will be accepted and the user will be warned about the need to install a new sensor.
In case all the technical requirements are fulfilled, an edition form, where the general data of the case may be typed, will be presented.
The following fields will become available:
Case History
First Name
Middle Name
Last Name
Age
Sex
Test date
Sample *
Description
Microorganism *
Area *
Doctor
Nosocomial
Deceased Two commands are now available:

Cancel: Returns to the ATB Menu.
OK: Selecting this option will take the user to the measuring environment where its case number identifies each antibiogram. A low frequency tone signal, together with an "Insert Sensor" message in the window's title bar, will instruct inserting the sensor in the first well, A higher frequency tone and a "Remove Sensor" message will indicate that the corresponding measurement has been done and that the sensor should be removed from the current well and inserted in the following. This procedure will be repeated for each well in the strip. The antibiotic set in use and the case number will be displayed in this window.

During measurements, the system constantly monitors any possible operation error, supplying instructions to solve any inconsistency that can arise.

The reading cycle is illustrated in the following diagram:

READING CYCLE
Message: Insert sensor+Low pitch tone=>Sensor inside the well+Reading result
Message: Remove sensor+High pitch tone=>Remove sensor from current well and move to next well. During measurements, the following actions are available:
- Previous: This option permits a new reading of the well, which is previous to the current well. It is used in order to correct reading errors.
- Next: Moves to the next well. The current reading will be ignored.
- Abort: Cancels the current antibiogram measurement.

When the complete set has been read, a new window with the results of the antibiogram will be shown, in which the bacterium's tolerance to each antibiotic is classified as SENSITIVE, INTERMEDIATE or RESISTANT. For each antibiotic under test, the inhibition percent is shown in units. The normalization algorithm will set to 1000 units, the standard value of the negative control well.

Three additional parameters, the Minimum Allowed Growth, the Growth Index and the Inhibition Factor will be taken into account in order to classify the results of the antibiograms according to three possibilities:

Successful Antibiogram: The measured data and the final results are reliable.
Not reliable Antibiogram:—The Minimum Allowed Growth has not been reached.
Useless Antibiogram: A mathematical analysis of the Inhibition Factor shows as abnormal data set.

URO-ATB
Links a uroculture to an antibiogram. This option is used when an antibiogram of a positive sample is made in order to obtain the patient's data. To select the case that will be tested, only the consecutive number and the date of the test are required. The designation URO-ATB and the corresponding consecutive number in the database of the uroculture then identify these cases.

McFarland
Activates the McFarland calibrator for the monitoring of microbial growth.

Database
Allows display and process of the stored data of antibiogram cases. The procedure is similar to the one described in the "UROCULTURE MENU" (Database).

Options
Same as in the URO Menu. Allows the following possibilities:

Automatic printout after antibiograms measurement.
Enable or disable the urocultures time-out sound signal.
The use of colors in the screen's report.
The time that will elapse between first and next uroculture readings. (4:00 hours is default in the program)

Antibiotics
Enables the operator to delete, modify or use an already existing set of antibiotics or to create a new one. The antibiotic design defined by the user must exactly match the antibiotic discs existing in the plate or strip. Selecting the "Antibiotics" option will bring the following possibilities:

New: Allows creation of a design for a new antibiotic set.

Upon selection, the user will be asked for the number of strips and the number of wells per strip in order to build up the corresponding design (Normally 2×8). Then a window will be displayed in order to fill in the name of the set and to select, from a supplied list, each of the antibiotics that will be used.

View: Allows display or printing of a specific set of antibiotics.
Modify: Changes the distribution or deletes antibiotics from a specific set.
Delete: Deletes a complete set of antibiotics.
Make current: This option predetermines the antibiotic set that will be used for the next antibiograms. To change the current setting, the desired set should be selected and the option "Make current" activated after the selection is done.
Select all: Selects every existing antibiotic set.
Unselect: Unselects every antibiotic set previously selected.
Return: Returns to the previous option.

Stability
This procedure is used to test the performance of the sensor.

Statistic parameters such as mean value, standard deviation and variance coefficient of a set of 16 identical samples are calculated. Results are stored in a specific database where they can be retrieved for viewing or printing at the option of the user.

To perform this test, distilled water is used for each of the 16 measurements.

The expected values for these statistical parameters are:

2000<Mean value:<3000

Standard Deviation<20

Variance coefficient<2.00

Clean Sensor
In addition to the systematic daily cleaning procedures indicated automatically by the system's software, an optional Sensor Cleaning Procedure can be carried out in which the duration of each step can be manually programmed. The complete cleaning cycle is composed of three basic steps:

1) A biologic detergent dilution is supplied to the flow sensor using the peristaltic pump.
2) Distilled water replaces the biologic detergent for rinsing the sensor.
3) A period of time passes in order to flush the complete system.

Calibrate
Executes the calibration procedure for the microflow sensor. In order to update the system's performance, calibration must be done each time a new sensor is installed or as indicated by the software.

Calibration is a procedure by means of which the response level of each sensor to a predetermined bacterial growth (0.5 McFarland) is established. It is not a daily routine, and it is recommended that calibration be done each time the software recommends this action in order to maintain a standardized response and sensitivity.

To perform calibration, inoculate a flask with *Staphylococcus aureus* with a 0.5 McFarland Growth Index (C+) in agreement with the system's McFarland calibrator. Use a second sterile culture medium flask to obtain a 0 McFarland Index (C−).

Select "Calibrate" from the ATB Menu and follow the interactive procedure to perform three alternate readings of a (C+) followed by a (C−).

The system will calculate a mean value for the three measurements; the final result will be stored after selecting "OK."

Flow Check

This auxiliary procedure helps the user by checking the amount and stability of the flow delivered by the peristaltic pump, since a lack of continuity or an incorrect flow may cause errors during the measurements.

The flow is checked using a 10-ml graduate probe and a recipient with distilled water.

To perform the check, both ends of the hose are inserted into a recipient filled with distilled water. "Proceed" command, available inside the "Flow check" option of the ATB Menu, is selected. The interactive procedure will be a guide throughout the process. Once finished, the obtained flow of about 2.4 ml/min should be verified.

If the expected volume is not reached, the cassettes tension lever and the tension of the silicone hose within the cassette should be checked. Also the technical conditions of the silicone hose, especially of the section inside the cassette which is in mechanical contact with the pump's rollers should be checked. If the hose is extremely collapsed or damaged, a new one should be installed.

Help

Shows information about the system and each option.

Return

Returns to the Main Menu.

Example 6

Results of the clinical trials carried out in Cuba:

A total of 567 urine samples were analyzed for the presence of a significant number of uropathogens, using the system of this invention, and matching the results with those obtained by reference method CLED (semiquantitative plate of culture method of Claridge). According to analysis 126 samples were positive by CLED, while 108 were positive using the present system in just 4 hours, while CLED method results were ready 24–48 hours after culture medium inoculation. The present system was 86.1% effective for detection of positive samples in only 4 hours after samples were inoculated.

From 441 samples found negative by CLED method, the present system was able to detect 440 negatives in a period of 4 hours, for an effectivity of 99.8%. The general correlation between present system and the traditional CLED method was 89.1%.

Example 7

Results of clinical trials carried out in Canada:

In total 1,016 urine samples have been investigated. Results obtained with the system were compared with the semiquantitative plate of culture method of Claridge, used as the reference method for the detection of bacterium. For routine culture, 0.001 ml of urine was delivered to a CLED agar plate using a calibrated disposable loop. This method detects >1000 colony forming units/ml (cfu/ml).

Turbidity readings were made at 0, 2, 3, 4 and 5 hours after inoculation. There were 184 samples with positive (>0.4 McFarland units). The time distribution and correlation with routine culture of these samples are shown in Table 1.

TABLE 1

| Time (hours) | Number detected | Correlation with Routine Culture % |
| --- | --- | --- |
| 2 | 32 | 97 |
| 3 | 80 | 88 |
| 4 | 52 | 87 |
| 5 | 20 | 65 |
| All | 184 | 86.4 |

Thus, the overall sensitivity of the present system was 86.4%, and the specificity (i.e. the ability to detect truly negative samples as defined by routine culture) was 98.5%.

BRIEF DESCRIPTION OF THE DRAWINGS

FIG. 5 shows two screens related to the program that follows the main procedures for the execution of the method subject of the present invention.

Figure 1:
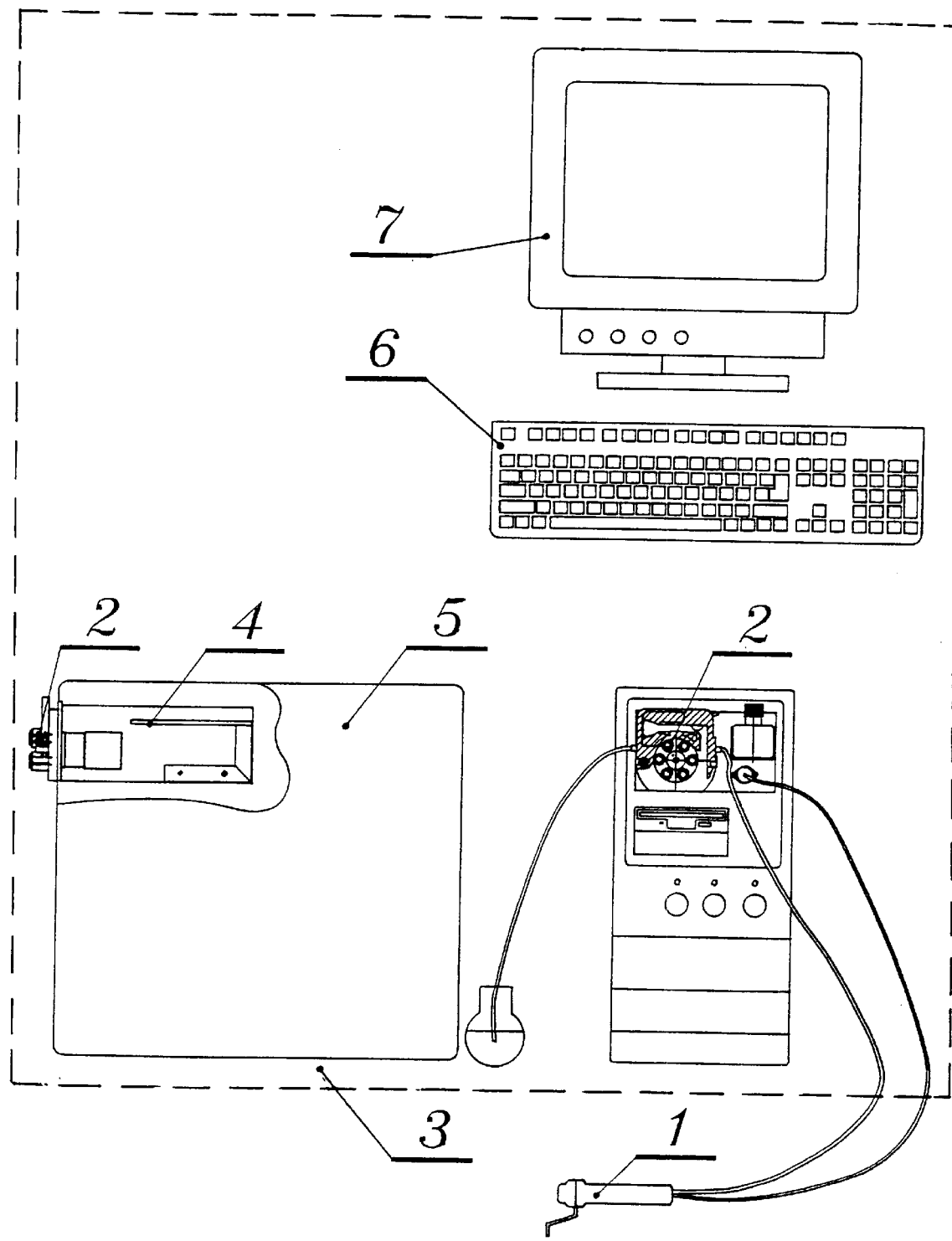
FIG. 1 shows the overview of the equipment of the present invention in a general overview. As shown, this equipment is based on a turbidimetric reader of microflow (1), which is fed by a peristaltic pump (2) and adjusted to electronic equipment of high sensitivity (3) that detects turbidimetric changes of (1) through a measuring method which permits use of a group of algorithms to detect small turbidimetric variations and process obtained data. It is formed by a turbidimetric measurement circuit (4) connected through an interface card to a central processing unit (5). This unit receives all keyboard commands (6) and delivers the results in a display (7). It can detect smallest variations of turbidity that occur in the inoculated culture medium of the sample that will be tested.
Figure 2:
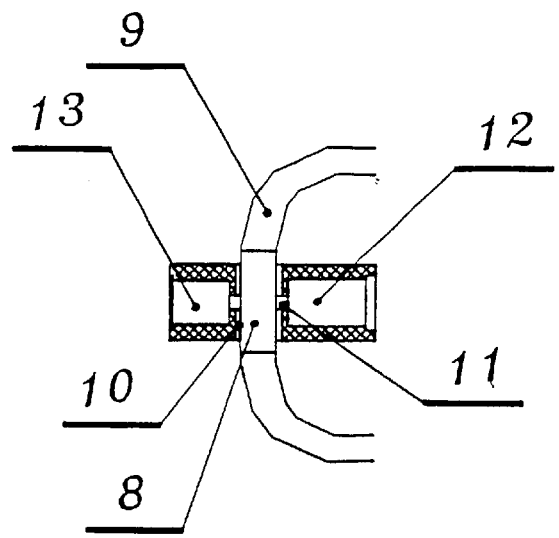
FIG. 2 represents a detailed view of the internal structure of the turbidimetric reader (1) of the FIG. 1. The small opening of the reader (8) is introduced into the sample to be tested which then circulates through it with help of the peristaltic pump (2) of the FIG. 1. The measurement chamber is composed of a plastic tube (9) introduced in a glass capillary (10). The light pass (11) is the diameter of the orifice through which the light coming from the photoemissor (12) traverses, arriving at the measurement chamber (9 and 10). The intensity of the luminous radiation transmitted through the measurement chamber (9 and 10) will depend on turbidity level of the sample and is measured by a photodetector (13). The radiation produced by the photoemissor (12) is stabilized by means of an electronic circuit of conventional automatic control.
Figure 4:
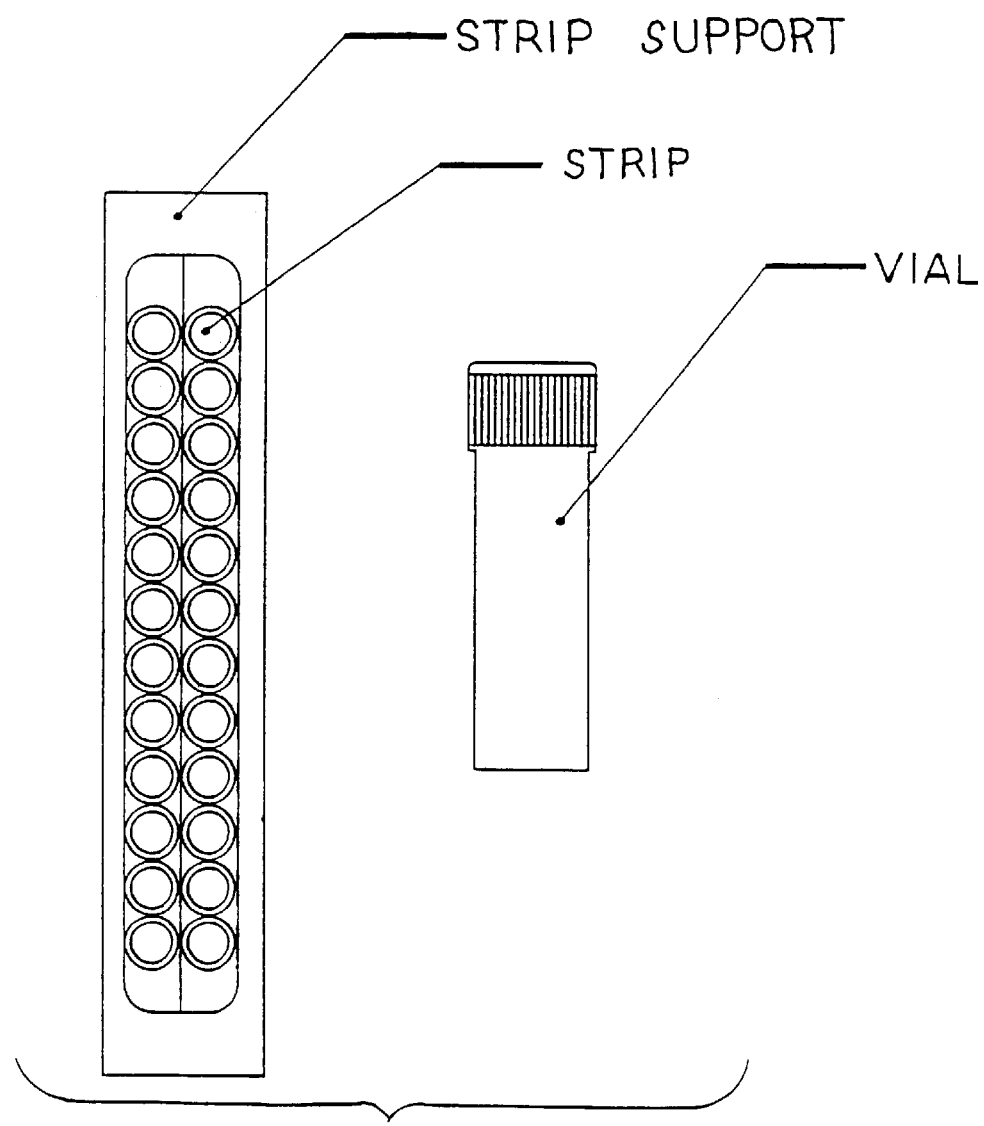
FIG. 4 shows the components of the diagnostic kit of the present invention, consisting of a vial containing culture medium and the polymer, the strip support and the strip used for antibiogram determination of the sample.
Figure 3:
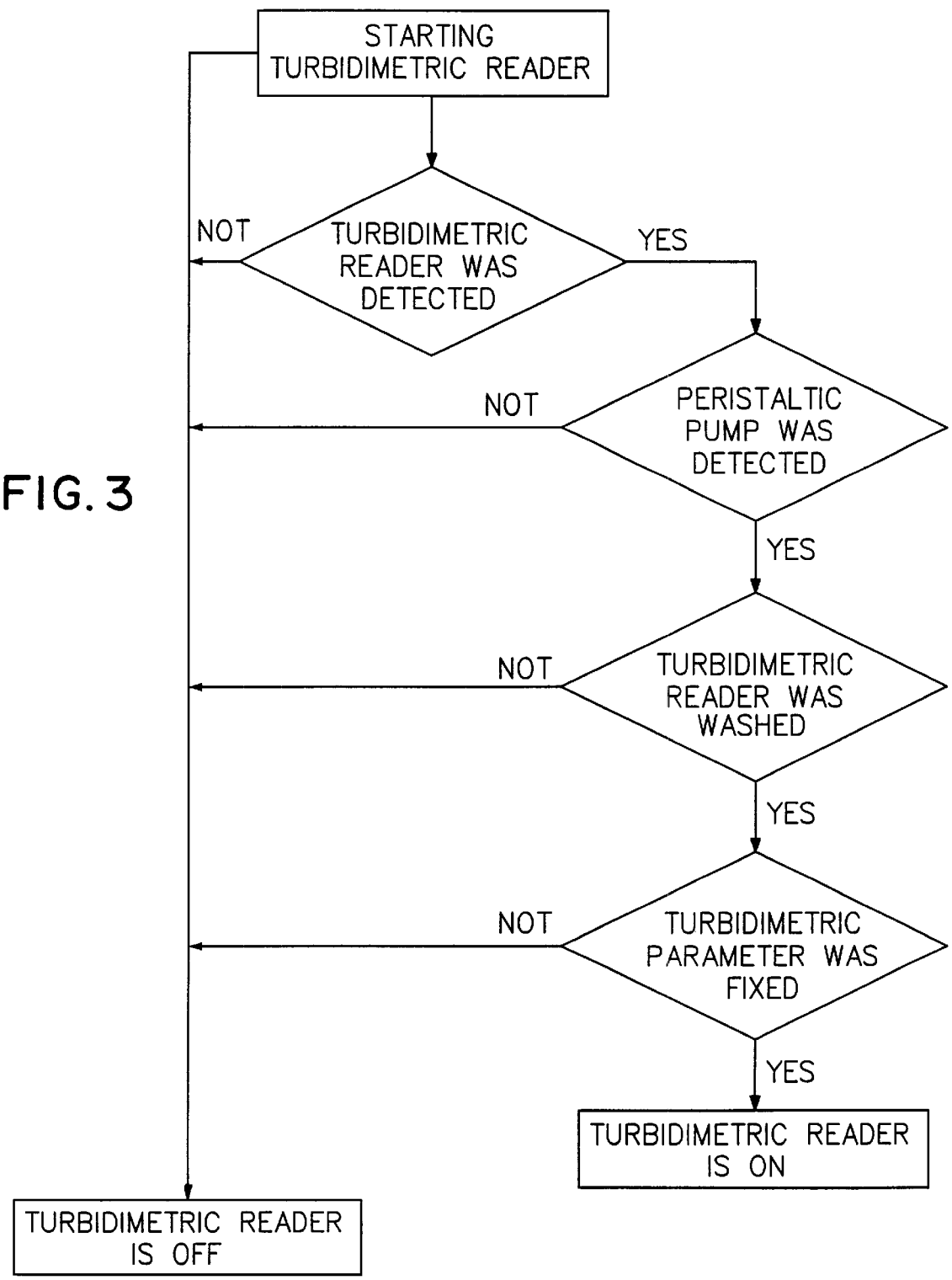
FIG. 3 shows turbidimetric reader proceeding through a diagram of flow. First, the presence of the turbidimetric reader is verified by means of the subroutine of detection. If present, the existence of the peristaltic pump is checked; the pump is necessary for turbidimetric reading and for cleaning execution subroutine. It also establishes the required working flow. When all the working parameters have been regulated, the turbidimetric reader will be ready. Any subroutine that is broken will disable the reader functioning.

Screen of Main Menu (5A): constitutes the starting point for all operations that are performed when these are activated.

Nine icons define the available options within the main menu which control the actions of the system. These are:

URO: Activates the icons menu of urocultures.
ATB: Activates the icons menu of the antibiogram.
McFarland: Permits measurement of the content of the vial in the calibration unit (McFarland scale).
Database: Permits access to the database of antibiograms or urocultures.
Options: Changes configuration of the system.
Information: Shows administrative information of the system.
DIPANIC: Gives the address of the producer of the system.
Help: Gives information on the current option.
Exit: Abandons the system.

Screen of Menu of Urocultures (5B): Represents a specific menu for the particular treatment of the urocultures that contains the operations to be performed during these tests, as a representation of the main options given by the Main Menu.

What is claimed is:

1. An apparatus for microbial diagnosis, comprising:
   a static turbidimetric reader for sensing a microflow which is fed by a peristaltic pump; and
   wherein the turbidimetric reader is coupled to a microcomputer using an interface card.

2. The apparatus according to claim 1, further including an additional device shaped by a UV lamp for the identificaiton of E.coli in analyzed samples.

3. The apparatus according to claim 1, wherein the turbidimetric reader includes a measurement chamber composed of a plastic tube introduced in a glass capillary, the measurement chamber being illuminated by a light passing therethrough for reading the sampling circulating therethrough.

4. The apparatus according to claim 3, wherein the turbidimetric reader includes a photodetector which measures the turbidity grade of the sample independent of the intensity of the radiation that it receives after light passes through the measurement chamber.

5. The apparatus according to claim 4, wherein the turbidimetric reader is coupled to electronic equipment including an electronic loop of automatic control to stabilize radiation emitted by a photoemissor.

6. The apparatus according to claim 5, wherein the electronic equipment detects, by means of a photodetector, the turbidity changes in the sample which circulates through the measurement chamber of the turbidimetric reader.

7. The apparatus according to claim 5, wherein the turbidimetric reader is connected to a central processing unit which receives all keyboard commands and delivers the results in a display.

8. The apparatus according to claim 1, wherein the turbidimetric reader is coupled to electronic equipment including an electronic loop of automatic control to stabilize radiation emitted by a photoemissor.

9. The apparatus according to claim 8, wherein the electronic equipment detects, by means of a photodetector, the turbidity changes in the sample which circulates through a measurement chamber of the turbidimetric reader.

10. The apparatus according to claim 8, wherein the turbidimetric reader and the microflow sensor are connected to a central processing unit which receives all keyboard commands and delivers results on a display.

11. A kit for microbial diagnosis, comprising:
    nontransparent strips including two free positions for positive and negative controls, and 10 to 22 positions where antibiotic discs can be placed according to a user's option;
    a glass vial containing a liquid culture medium and a polymer; and
    an additional vial containing a reagent for the development of the enzymatic activity.

12. The kit according to claim 11, wherein the vial contains enzymatic substrates for E.coli identification and additives to improve the enzymatic activity.

13. The kit according to claim 11, wherein the liquid culture medium is modified liquid medium Muller Hinton (OXOID).

14. The kit according to claim 11, wherein the polymer added to the liquid culture medium is any lineal polysaccharide of structural formula CH3-CH3-CH3-N, molecular weight about 50,000 and 150,000, which is added to the liquid culture medium in a concentration in the range between 0.05 and 1%.

15. The kit according to claim 11, wherein the vial containing the liquid culture medium and the polymer contains the substrates MU-(Dglucoronid and L-Triptophane), both solubilized in potassium phosphate 50 mM, pH 70 to 7.5.

16. The kit according to claim 11, wherein the developer reagent used is modified Kovacks reagent constituted by 2 g of paradimethylaminobenzaldehyde diluted in ethanol and 20 ml of concentrated Chlorhydric Acid.

17. A method for microbial diagnosis which comprises the following steps:
    a) inoculating an aliquot of a sample directly obtained from its source in a glass vial containing a culture medium and a polymer;
    b) determining the turbidity of the vial to time=0;
    c) incubating the vial between 2 and 6 hours to a temperature between 35° C. and 37° C.;
    d) determining the growth index between time 0 and the selected time of incubation, and discriminating positive samples from negative samples in dependence of the increase of the turbidity, being positives those samples with increases higher than 0.08 McFarland units, from which aliquots are taken for further steps.

18. The method according to claim 17, wherein for antibiogram execution the following further steps are performed:
    an aliquot of a positive sample is taken from step c) and transferred to a new glass vial containing fresh culture medium, which is dispensed in a rate of 200 µl in each well of the strip and is incubated between 3 to 4 hours to a temperature between 35 and 37° C.;
    the plate is read by placing the microflow sensor in each well;
    the new vial is read by the microflow sensor to identify density values;
    the growth index is then calculated from the density values obtained in the controls, and the inhibitions percentages are calculated for each sample of each antibiotic;
    according to the level obtained, the criterion of sensibility is adjusted for those samples showing inhibition between 60 and 100%, which previously have been checked for inclusion of this result between the minimum and maximum values of growth admissible for said microorganism;
    the results obtained in the previous steps and the data edited for each sample are passed automatically to create a database for establishing antibiogram.

19. The method according to claim 17, wherein to identify positive samples infected by E.coli the following steps are performed:
    an aliquot is taken from step c) and submitted to a source of UV light to detect the fluoresce generated due to 4-methylumbeliferone liberation and to develop Indol formation using modified Kovacks reagent;

for those samples did not identified as *E.coli* in the step of taking an aliquot, the aliquot previously obtained in the step c) is submitted to the traditional process of isolation and identification.

20. The method according to claim 17, wherein the step of inoculating includes using a vial further including substrates selected and the necessary additives for *E.coli* identification.

* * * * *